United States Patent [19]

Hensen et al.

[11] Patent Number: 4,744,924

[45] Date of Patent: May 17, 1988

[54] COSMETIC DETERGENT BASE

[75] Inventors: Hermann Hensen, Hilden; Dagmar Stuhrmann, Duesseldorf; Renate Lindner, Hilden; Renate Kruse, Duesseldorf, all of Fed. Rep. of Germany

[73] Assignee: Henkel Kommanditgesellschaft auf Aktien, Duesseldorf, Fed. Rep. of Germany

[21] Appl. No.: 69,789

[22] Filed: Jul. 2, 1987

[30] Foreign Application Priority Data

Jul. 4, 1986 [DE] Fed. Rep. of Germany ....... 3622438

[51] Int. Cl.$^4$ .............................................. C11D 1/29
[52] U.S. Cl. ..................................... 252/551; 252/117; 252/174.21; 252/531; 252/532; 252/550; 252/544; 252/DIG. 5; 252/DIG. 13; 252/DIG. 14
[58] Field of Search ................... 252/117, 174.21, 531, 252/532, 550, 551, 544, DIG. 5, DIG. 13, DIG. 14

[56] References Cited

U.S. PATENT DOCUMENTS

| 4,092,272 | 5/1978 | Nishimura et al. | 252/551 |
| 4,384,978 | 5/1983 | Ploog et al. | 252/550 |
| 4,483,787 | 11/1984 | Jones et al. | 252/551 |

FOREIGN PATENT DOCUMENTS 2158456 11/1985 United Kingdom .

Primary Examiner—Paul Lieberman
Assistant Examiner—Hoa Van Le
Attorney, Agent, or Firm—Ernest G. Szoke; Henry E. Millson, Jr.

[57] ABSTRACT

A detergent base showing good compatibility with the skin in the form of a fluid concentrate containing from 0.4 to 0.6 mole/kg of an alkyl ether sulfate based on a special mixture of fatty alcohol ethoxylates which is present partly as magnesium salt and partly as sodium salt, from 0.03 to 0.08 mole/kg of an oleic acid diethanolamide and/or linoleic acid diethanolamide and from 1.4 to 1.6 mole/kg sodium ions in the form of sodium chloride and/or sodium sulfate. The product is suitable for use in cosmetic hair and body shampoos.

2 Claims, No Drawings

COSMETIC DETERGENT BASE

BACKGROUND OF THE INVENTION

1. Field of the Invention

This invention relates to a new base for cosmetic detergents which contains alkyl ether sulfate surfactants, and which exhibits particular flow properties based on the presence of special fatty acid alkanolamides and of sodium and magnesium ions.

2. Statement of Related Art

In addition to good cleaning power, cosmetic detergent bases suitable for the production of liquid hair and body shampoos have to show good foaming power and good compatibility with the skin and mucous membrane. In addition, it is a considerable advantage if a detergent base of this type remains fluid and pumpable, even at high concentrations, but does not become too thinly liquid after dilution to the in-use concentration or which may still be effectively thickened, so that the shampoo does not run through the fingers like water in use.

It was known that alkyl ether sulfates, particularly in the form of their magnesium salts, are distinguished by particularly good compatibility with the skin and mucous membrane. This applies especially to ether sulfates having a high degree of ethoxylation. Unfortunately, however, the foaming power and the viscosity and thickenability of the dilute solutions by electrolytes decreases with increasing degree of ethoxylation. It is also known that the viscosity and thickenability of dilute solutions of surfactants can be increased with fatty acid alkanolamides. However, in solutions of relatively high concentration of the type commonly and economically required for the detergent bases, an addition of fatty acid alkanolamides leads readily to gel formation and to loss of pumpability.

STATEMENT OF THE INVENTION

Other than in the operating examples, or where otherwise indicated, all numbers expressing quantities of ingredients or reaction conditions used herein are to be understood as modified in all instances by the term "about".

An object of the present invention is to provide a cosmetic detergent base showing high compatibility with the skin and mucous membrane, good pumpability and good foaming power which, even after dilution to a fraction of the starting concentration, may be rethickened by addition of an electrolyte, for example sodium chloride.

It has been found that these requirements are met by a cosmetic detergent base in the form of an aqueous concentrate pumpable at 20° C. which contains from 0.4 to 0.6 mole/kg of an alkyl ether sulfate mixture of sulfated ethoxylates consisting of from 35 to 45% by weight of an adduct of 8 to 12 moles ethylene oxide per mole of a substantially linear $C_{12}$–$C_{18}$ fatty alcohol cut, from 40 to 60% by weight of an adduct of 1 to 3 moles ethylene oxide per mole of a substantially linear $C_{12}$–$C_{14}$ fatty alcohol cut, from 0 to 20% by weight of an adduct of 1 to 3 moles ethylene oxide per mole of an oleyl/cetyl alcohol mixture, of which from 0.2 to 0.3 mole is present as magnesium salt and the rest as sodium salt, from 0.03 to 0.08 mole/kg oleic acid diethanolamide and/or linoleic acid diethanolamide and from 1.4 to 1.6 moles/kg sodium ions in the form of sodium chloride and/or sodium sulfate and, for the rest, essentially water. The detergent base according to the invention not only is distinguished by particularly good compatibility with mucous membrane and by good foaming power, but also undergoes a 3 to 4 fold increase in viscosity on dilution with approximately 20 parts water to 100 parts of the detergent base. Aqueous solutions containing 10% by weight anionic surfactant may be thickened to viscosities of from 5,000 to 10,000 mPa.s (20° C.) by addition of sodium chloride.

The detergent base according to the invention is produced very easily by initially combining the ethoxylates and determining the hydroxyl number (i.e. the molecular weight) of the mixture.

The adduct of 8 to 12 moles ethylene oxide with a substantially linear $C_{12}$–$C_{18}$ fatty alcohol cut is prepared in known manner by ethoxylation of a suitable fatty alcohol, for example a coconut oil or palm kernel oil fatty alcohol cut containing from 12 to 18 carbon atoms. Coconut oil fatty alcohol cuts such as these contain for example from 0 to 3% by weight n-decanol, from 45 to 60% by weight n-dodecanol, from 15 to 30% by weight n-tetradecanol, from 6 to 15% by weight n-hexadecanol and from 10 to 15% by weight n-octadecanol.

The adduct of 1 to 3 moles ethylene oxide with a substantially linear $C_{12}$–$C_{14}$ fatty alcohol cut is similarly prepared, for example, from a coconut oil or palm kernel oil fatty alcohol cut containing from 12 to 14 carbon atoms. Fatty alcohol cuts such as these contain, for example, from 0 to 2% by weight n-decanol, from 70 to 75% by weight n-dodecanol, from 25 to 30% by weight n-tetradecanol and from 0 to 5% by weight n-hexadecanol.

Instead of the saturated coconut oil or palm kernel oil fatty alcohols, it is also possible to use synthetic, unbranched or only slightly branched fatty alcohols, provided at least 90% by weight thereof consists of the specified C-chain lengths.

The quantity of sodium salt to be added in the preparation of the detergent base of the invention is best determined by determination of the $Cl^{(-)}$ and $SO_4^{(--)}$ ions present in the product after neutralization. If the product contains, for example, x moles/kg $Cl^{(-)}$ and y moles/kg $SO_4^{(--)}$ ions, $1.5-(x+2y)$ moles sodium chloride for example has to be added to adjust the detergent base to a content of 1.5 moles sodium ions.

The detergent base according to the invention is distinguished by particularly favorable viscosity behavior, by good foaming power and by good compatibility with the mucous membrane of the eyes. These properties are of particular advantage where the alkyl ether sulfate present consists of sulfated ethoxylates consisting of from 40 to 45% by weight of an adduct of 10 moles ethylene oxide per mole of a $C_{12}$–$C_{18}$ coconut oil fatty alcohol cut, from 40 to 50% by weight of an adduct of 2 moles ethylene oxide per mole of a $C_{12}$–$C_{14}$ coconut oil fatty alcohol cut and from 8 to 12% by weight of an adduct of 2 moles ethylene oxide per mole of an oleyl/cetyl alcohol mixture.

The detergent base according to the invention is especially suitable for the production of high-foam cosmetic hair and body shampoos compatible with the skin.

The invention will be illustrated but not limited by the following examples.

EXAMPLES 1.1 A mixture of 96 kg of an adduct of 10 moles ethylene oxide with a $C_{12}$–$C_{18}$ coconut oil fatty alcohol (54% by weight $C_{12}$, 22% by weight $C_{14}$, 10% by weight $C_{16}$, 12% by weight $C_{18}$), 113 kg of an adduct of 2 moles ethylene oxide with a $C_{12}$–$C_{14}$ coconut oil fatty alcohol (73% by weight $C_{12}$, 27% by weight $C_{14}$) and 24.5 kg of an adduct of 2 moles ethylene oxide with an oleyl/cetyl alcohol (65% by weight $C_{18}$, 30% by weight $C_{16}$, 5% by weight $C_{14}$, iodine number 50) was reacted with 74.4 kg chlorosulfonic acid at 10° to 20° C. in a continuous reactor to form the sulfuric acid semiester and then neutralized with 55.5 kg of a 50% aqueous sodium hydroxide solution. The alkyl ether sulfate obtained had an anionic surfactant content of 0.592 moles/kg (as determined by two-phase titration by DGF-Einheitsmethode H-III-10).

1.2 28.2 g $MgSO_4.7H_2O$ (0.114 mole), 20 g oleic acid diethanolamide, 4.6 g trisodium citrate, 65 g sodium chloride (1.1 moles) and 2.2 kg water were added to 880 g of the ether sulfate of 1.1. A liquid detergent base having an anionic surfactant content of 0.59 mole/kg corresponding to approximately 28% by weight (calculated for an average molecular weight of the anionic surfactants of 475) was obtained.

2. Testing of viscosity behavior 2.1 Viscosity as a function of concentration

| Concentration (anionic surfactant content) | Viscosity at 20° C. (Hoppler falling ball viscosimeter) |
| --- | --- |
| 0.59 mole/kg | 7,500 mPa.s |
| 0.54 mole/kg | 21,500 mPa.s |
| 0.49 mole/kg | 31,500 mPa.s |
| 0.44 mole/kg | 23,200 mPa.s |
| 0.39 mole/kg | 7,000 mPa.s |

2.2 Thickenability by addition of NaCl

| Concentration (anionic surfactant content) | NaCl added (% by weight) | Viscosity at 20° C. (Hoppler falling ball viscosimeter) |
| --- | --- | --- |
| 0.2 mole/kg | — | 300 mPa.s |
| 0.2 mole/kg | 6 | 1,200 mPa.s |
| 0.2 mole/kg | 7 | 5,600 mPa.s |
| 0.2 mole/kg | 8 | 8,000 mPa.s |
| 0.2 mole/kg | 9 | 12,000 mPa.s |

What is claimed is:

1. A cosmetic detergent base in the form of an aqueous concentrate pumpable at 20° C., comprising
   from about 0.4 to about 0.6 mole/kg of an alkyl ether sulfate mixture of sulfated ethoxylates consisting of
   from about 35 to about 45% by weight of an adduct of 8 to 12 moles ethylene oxide with one mole of a substantially linear $C_{12}$–$C_{18}$ fatty alcohol cut,
   from about 40 to about 60% by weight of an adduct of 1 to 3 moles ethylene oxide with one mole of a substantially linear $C_{12}$–$C_{14}$ fatty alcohol cut,
   from 0 to about 20% by weight of an adduct of 1 to 3 moles ethylene oxide with one mole of an oleyl/cetyl alcohol mixture, of which about 0.2 to about 0.3 mole is present as magnesium salt and the rest as as sodium salt,
   from about 0.03 to about 0.08 mole/kg oleic acid diethanolamide and/or linoleic acid diethanolamide and
   from about 1.4 to about 1.6 moles/kg sodium ions in the form of sodium chloride and/or sodium sulfate.

2. The cosmetic detergent base of claim 1, wherein the sulfated ethoxylates consist of
   from about 40 to about 45% by weight of an adduct of 10 moles ethylene oxide with one mole of a $C_{12}$–$C_{18}$ coconut oil fatty alcohol cut,
   from about 40 to about 50% by weight of an adduct of 2 moles ethylene oxide with one mole of a $C_{12}$–$C_{14}$ coconut oil fatty alcohol cut and
   from about 8 to about 12% by weight of an adduct of 2 moles ethylene oxide with one mole of an oleyl/cetyl alcohol mixture.

* * * * *